US012758203B2

(12) United States Patent
Nadzadi et al.

(10) Patent No.: US 12,758,203 B2
(45) Date of Patent: Oct. 13, 2026

(54) SURGICAL TOOL GUARD

(71) Applicant: MAKO Surgical Corp., Weston, FL (US)

(72) Inventors: Mark Ellsworth Nadzadi, Batavia, OH (US); Andrew Jacob Nelson, New York City, NY (US); Jeremiah Beers, Evergreen, CO (US); Matthew Joseph Guthart, Miami, FL (US)

(73) Assignee: MAKO Surgical Corp., Weston, FL (US)

( * ) Notice: Subject to any disclaimer, the term of this patent is extended or adjusted under 35 U.S.C. 154(b) by 654 days.

(21) Appl. No.: 17/862,804

(22) Filed: Jul. 12, 2022

(65) Prior Publication Data

US 2023/0013867 A1 Jan. 19, 2023

Related U.S. Application Data

(60) Provisional application No. 63/223,103, filed on Jul. 19, 2021.

(51) Int. Cl.
*A61B 17/00* (2006.01)
*A61B 34/30* (2016.01)
(Continued)

(52) U.S. Cl.
CPC ................... *A61B 17/00234* (2013.01); *A61B 2017/00367* (2013.01); *A61B 2034/305* (2016.02)

(58) Field of Classification Search
CPC ........ A61B 17/00234; A61B 17/32002; A61B 2017/00367; A61B 2034/305;
(Continued)

(56) References Cited

U.S. PATENT DOCUMENTS 2,429,356 A 10/1947 Hicks
3,384,085 A 5/1968 Hall
(Continued)

FOREIGN PATENT DOCUMENTS

BR 302014001911 5/2015
CN 113040865 A * 6/2021 ........ A61M 25/0045
(Continued)

OTHER PUBLICATIONS

English language abstract and machine-assisted English translation for DE 10 2012 207 332 A1 extracted from espacenet.com database on Jul. 13, 2022, 11 pages.
(Continued)

*Primary Examiner* — Tan-Uyen T Ho
*Assistant Examiner* — Lindsey R. Rivers
(74) *Attorney, Agent, or Firm* — Howard & Howard Attorneys PLLC

(57) ABSTRACT

A guard for a tool. The tool is actuatable by a surgical device and has an elongated member and an energy applicator disposed at a distal end of the elongated member. The guard may have a monolithic body including a proximal end and a distal end opposite the proximal end. The proximal end connects to the surgical device. The body further has an interior surface defining a bore extending between the proximal and distal end and the bore adapted to receive the elongated member therethrough and an exterior surface extending between the proximal and distal end and encompassing the interior surface between the proximal and distal end. The body has at least one thermal mitigation channel located between the interior and exterior surfaces and opening through at least one port in the exterior surface.

18 Claims, 7 Drawing Sheets

(51) Int. Cl.
*A61B 17/32* (2006.01)
*A61B 90/00* (2016.01)

(58) Field of Classification Search
CPC ... A61B 90/08; A61B 2090/0801; A61B 1/12; A61B 1/121; A61B 1/122; A61B 1/123; A61B 1/125; A61B 1/126; A61B 1/127; A61B 1/128; A61B 1/00135; A61M 25/00; A61M 25/0015; A61M 25/0029; A61M 2025/018; A61M 39/02; A61M 39/0247; A61M 2039/0264; A61M 2039/0273; A61M 2039/0279; A61M 2039/0282; A61M 2039/082; A61M 25/0026; A61M 25/003; A61M 25/0071; A61M 2025/0003; A61M 2025/0004; A61M 2025/0006; A61M 2025/0037; A61M 2025/0039; A61M 2025/004; A61M 2025/0046; A61M 2025/0047; A61M 2025/0062
See application file for complete search history.

(56) References Cited

U.S. PATENT DOCUMENTS

| | | | |
|---|---|---|---|
| 3,937,222 A | | 2/1976 | Banko |
| D241,984 S | | 10/1976 | Lahay |
| 4,184,692 A | | 1/1980 | Benson et al. |
| D299,865 S | | 2/1989 | Kamstrup-Larsen et al. |
| 5,222,956 A | | 6/1993 | Waldron |
| D342,136 S | | 12/1993 | Lafferty et al. |
| 5,354,265 A | * | 10/1994 | Mackool ............. A61F 9/00745 606/128 |
| 5,494,359 A | | 2/1996 | Del Rio et al. |
| 5,630,818 A | | 5/1997 | Del Rio et al. |
| 5,651,783 A | | 7/1997 | Reynard |
| 5,833,704 A | | 11/1998 | McCombs et al. |
| 5,888,200 A | | 3/1999 | Walen |
| 5,941,887 A | | 8/1999 | Steen et al. |
| 5,984,904 A | | 11/1999 | Steen et al. |
| 6,171,300 B1 | | 1/2001 | Adams |
| 6,342,061 B1 | | 1/2002 | Kauker et al. |
| 6,428,501 B1 | | 8/2002 | Reynard |
| 6,706,023 B1 | | 3/2004 | Huttner et al. |
| 7,001,391 B2 | | 2/2006 | Estes et al. |
| 7,204,820 B2 | | 4/2007 | Akahoshi |
| 7,238,021 B1 | | 7/2007 | Johnson |
| D549,824 S | | 8/2007 | Sauer |
| 7,465,309 B2 | | 12/2008 | Walen |
| 7,998,159 B2 | | 8/2011 | Edwards |
| 8,523,866 B2 | | 9/2013 | Sidebotham et al. |
| D692,133 S | | 10/2013 | Steinwachs et al. |
| 8,821,085 B2 | | 9/2014 | Haimer et al. |
| 8,906,010 B2 | | 12/2014 | Edwards et al. |
| 8,961,519 B2 | | 2/2015 | Gillard et al. |
| 9,002,426 B2 | | 4/2015 | Quaid et al. |
| 9,008,757 B2 | | 4/2015 | Wu |
| D737,444 S | | 8/2015 | Mueller |
| 9,113,917 B2 | | 8/2015 | del Rio et al. |
| 9,119,655 B2 | | 9/2015 | Bowling et al. |
| 9,155,545 B2 | | 10/2015 | Prescott |
| 9,186,157 B2 | | 11/2015 | Brunnett et al. |
| 9,271,740 B2 | | 3/2016 | Scianamblo |
| 9,339,345 B2 | | 5/2016 | Song et al. |
| 9,414,848 B2 | | 8/2016 | Edwards et al. |
| D776,813 S | | 1/2017 | Evans |
| 9,566,121 B2 | | 2/2017 | Staunton et al. |
| 9,707,043 B2 | | 7/2017 | Bozung |
| 9,848,891 B2 | | 12/2017 | Berberich |
| 9,937,058 B2 | | 4/2018 | Axelson, Jr. et al. |
| D842,991 S | | 3/2019 | Cable |
| 10,363,615 B2 | | 7/2019 | Scianamblo |
| 10,413,305 B2 | | 9/2019 | Magno et al. |
| D881,386 S | | 4/2020 | Tiedeken et al. |
| 10,675,050 B2 | | 6/2020 | Staunton et al. |
| 10,675,054 B2 | | 6/2020 | Batchelor et al. |
| D893,027 S | | 8/2020 | Peters et al. |
| D900,997 S | | 11/2020 | Ancerewicz |
| 10,856,930 B1 | | 12/2020 | Trudel et al. |
| D908,216 S | | 1/2021 | Messerly et al. |
| D910,168 S | | 2/2021 | Sussman |
| D934,425 S | | 10/2021 | Kehren-Quitsdorf et al. |
| 11,224,427 B2 | | 1/2022 | Shelton et al. |
| D953,522 S | | 5/2022 | Scott |
| 11,525,476 B2 | | 12/2022 | Nishio |
| D1,021,090 S | | 4/2024 | Kor |
| D1,064,269 S | | 2/2025 | Zhang |
| 2003/0135151 A1 | * | 7/2003 | Deng .................. A61M 1/7413 604/32 |
| 2006/0241628 A1 | | 10/2006 | Parak |
| 2011/0092888 A1 | | 4/2011 | Gerg |
| 2014/0276949 A1 | | 9/2014 | Staunton et al. |
| 2015/0230821 A1 | | 8/2015 | Batchelor et al. |
| 2017/0319217 A1 | | 11/2017 | Manley et al. |
| 2018/0125607 A1 | | 5/2018 | Zastrow |
| 2019/0000472 A1 | | 1/2019 | Shelton et al. |
| 2019/0150954 A1 | | 5/2019 | Xie |
| 2019/0216497 A1 | | 7/2019 | Doerr et al. |
| 2019/0264850 A1 | | 8/2019 | Patrick et al. |
| 2020/0069316 A1 | | 3/2020 | DeSoutter et al. |
| 2021/0100563 A1 | | 4/2021 | Sansoucy et al. |
| 2021/0212714 A1 | | 7/2021 | Nguyen |
| 2022/0039898 A1 | | 2/2022 | Ding et al. |
| 2022/0304722 A1 | | 9/2022 | Nakano et al. |
| 2022/0330951 A1 | | 10/2022 | Cushen et al. |
| 2022/0338883 A1 | | 10/2022 | Hoegerle et al. |
| 2023/0013867 A1 | | 1/2023 | Nadzadi et al. |
| 2023/0181881 A1 | | 6/2023 | Sharma et al. |
| 2023/0255645 A1 | | 8/2023 | Best et al. |
| 2024/0390000 A1 | | 11/2024 | Mata et al. |
| 2025/0302572 A1 | | 10/2025 | Gsellman et al. |

FOREIGN PATENT DOCUMENTS

| | | | |
|---|---|---|---|
| DE | 202005008943 | U1 | 8/2005 |
| DE | 102012207332 | A1 | 11/2013 |
| EP | 3585331 | A1 | 1/2020 |
| JP | 2003111751 | | 3/2002 |
| WO | 9816155 | A1 | 4/1998 |
| WO | 2017152266 | A1 | 9/2017 |
| WO | 2018075935 | A1 | 4/2018 |
| WO | 2019064038 | A1 | 4/2019 |
| WO | 2020020898 | A1 | 1/2020 |
| WO | 2021011646 | A2 | 1/2021 |
| WO | 2021083567 | A1 | 5/2021 |
| WO | 2022063390 | A1 | 3/2022 |
| WO | 2022238541 | A1 | 11/2022 |

OTHER PUBLICATIONS

English language abstract and machine-assisted English translation for DE 20 20025 008 943 U1 extracted from espacenet.com database on Jul. 13, 2022, 4 pages.

English language abstract and machine-assisted English translation for WO 2019/064038 A1 extracted from espacenet.com database on Jul. 13, 2022, 8 pages.

Stryker Mako, “PKA Application User Guide”, PN209707, Rev. 3, Jun. 2018, 108 pages.

Stryker Mako, “PKA Application User Guide”, PN210712, Rev. 00, Mar. 2015, 104 pages.

English language abstract and machine-assisted English translation for WO 2022/063390 A1 extracted from espacenet.com database on Feb. 28, 2023, 16 pages.

English language abstract and machine-assisted English translation for WO 2022/238541 A1 extracted from espacenet.com database on Feb. 28, 2023, 28 pages.

Youtube, “Arthrex Mission and Core Value”, <https://www.youtube.com/watch?v=IQ4pqMXLT10,> Feb. 3, 2022, 3 pages.

Youtube, “Dominic Marino, DO—Mako Robotic-Arm Assisted Hip Replacement Surgery”, Halifax Health, https://www.youtube.com/watch?v=NfDCQ-Wfec, Feb. 3, 2022, 3 pages.

(56) References Cited

OTHER PUBLICATIONS

Youtube, "Robotics-Assisted Knee Replacement Surgery Using the CORI Surgical System", <https://www.youtube.com/watch?v=bSQsQXllolg,> Feb. 11, 2021, 3 pages.

* cited by examiner

FIG. 5
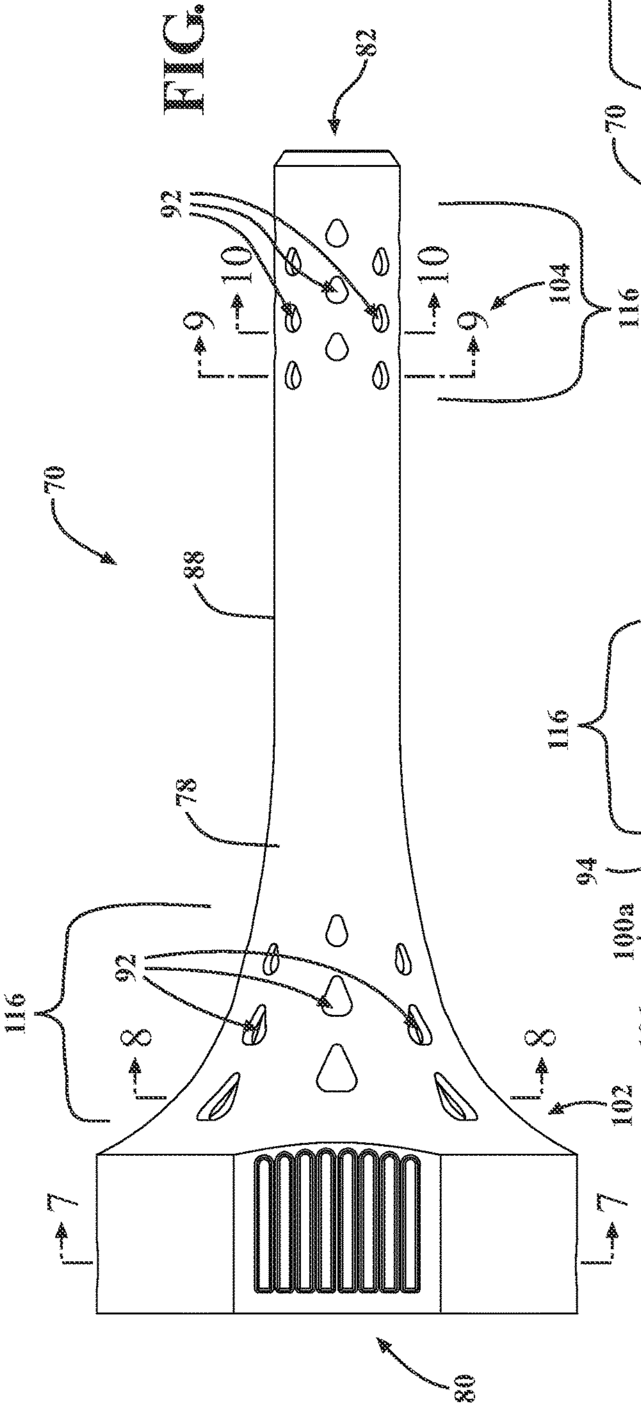
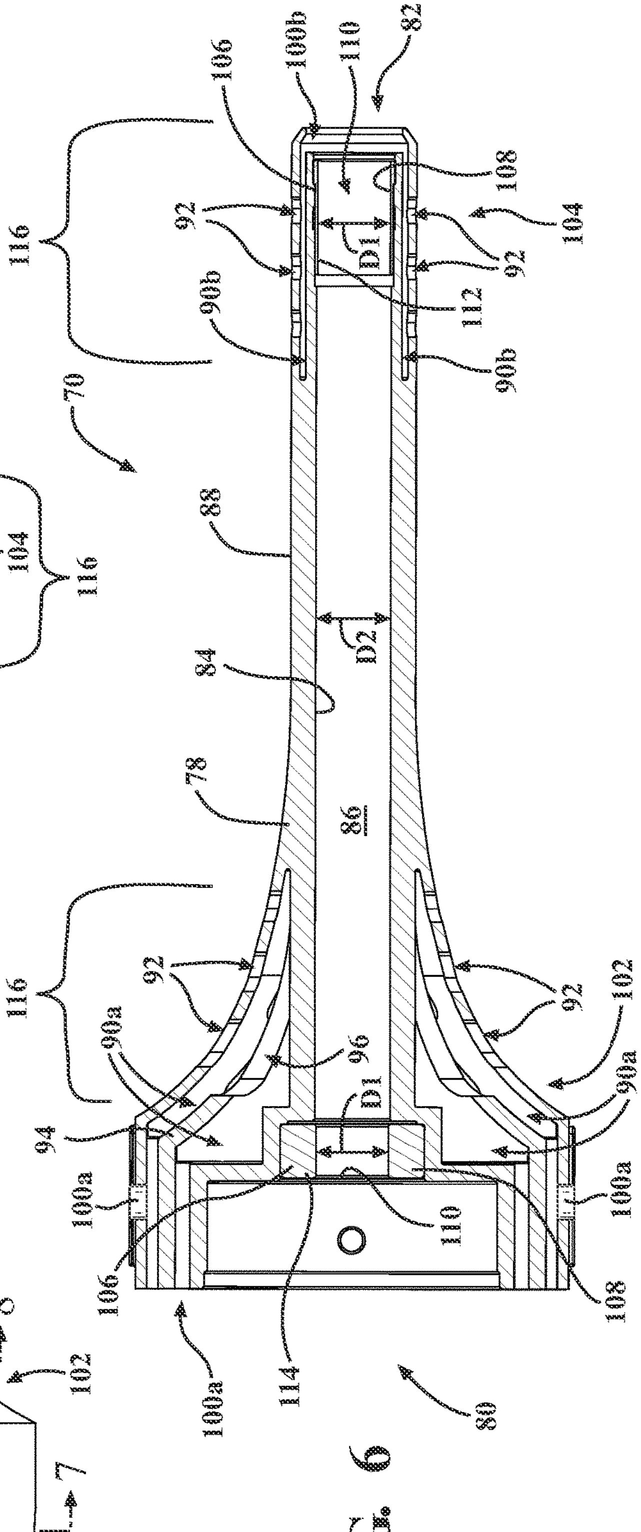
FIG. 6

SURGICAL TOOL GUARD

CROSS-REFERENCE TO RELATED APPLICATIONS

The subject application is a United States Non-provisional Patent Application claiming priority to and all benefits of U.S. Provisional Patent App. No. 63/223,103, filed on Jul. 19, 2021, the contents of which are hereby incorporated by reference in their entirety.

TECHNICAL FIELD

The present disclosure relates generally to a guard for a tool that is configured to be actuated by a surgical device.

BACKGROUND

Robotic systems are commonly used to perform surgical procedures and typically include a robotic device, such as robotic manipulator arm or a hand-held robotic device, comprising an end effector with a surgical tool coupled to and actuated by the robotic device.

In some conventional systems, the end effectors utilize a guard to support the tool and the protect the surgeon and/or patient tissue from contacting the actuated tool during or in preparation for a procedure. While the guards do support the tool and protect the user, they often absorb a large amount of heat from the actuated tool. Excessive heat build-up can cause damage to the patient's tissue. Furthermore, excess heat potentially can cause a burn risk to the patient, the operator that is manipulating the end effector, and/or to personnel who may otherwise grasp the end effector or tool (e.g., for removing or swapping the tool).

The excess heat may have detrimental effects on the tool, the guard, and the end effector as well. More specifically, excess heat can affect the material characteristics of the component, such as the temper of metallic components. Excess heat can also cause components to expand into contact with one another causing undesired friction or potential seizing, which can damage the contacting components as well as the components generating the movement, such as an electric motor. Furthermore, while the excess heat may not cause a catastrophic failure in every situation, the thermal cycling endured by the components through repeated high heat application can reduce the longevity of the components.

As such, there is a need in the art for guards that address at least the aforementioned problems.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a guard for a tool is provided that is configured to be actuated by a surgical device, with the tool comprising an elongated member and an energy applicator disposed at a distal end of the elongated member, the guard comprising: a monolithic body including: a proximal end and a distal end opposite the proximal end, the proximal end configured to connect to the surgical device; an interior surface defining a bore extending between the proximal end and the distal end and the bore adapted to receive the elongated member therethrough; an exterior surface extending between the proximal end and the distal end and encompassing the interior surface between the proximal end and the distal end; and at least one thermal mitigation channel located between the interior surface and the exterior surface and opening through at least one port in the exterior surface.

According to a second aspect, a guard for a tool is provided that is configured to be actuated by a surgical device, with the tool comprising an elongated member and an energy applicator disposed at a distal end of the elongated member, the guard comprising: a body including: a proximal end and a distal end opposite the proximal end, the proximal end configured to connect to the surgical device; an interior surface defining a bore extending between the proximal end and the distal end and the bore adapted to receive the elongated member therethrough; an exterior surface extending between the proximal end and the distal end and encompassing the interior surface between the proximal end and the distal end; and two thermal mitigation channels being adjacent to one another and located between the interior and exterior surfaces, and wherein an intermediate wall extends between the two thermal mitigation channels to separate the two thermal mitigation channels.

According to a third aspect, a guard for a tool is provided that is configured to be actuated by a surgical device, with the tool comprising an elongated member and an energy applicator disposed at a distal end of the elongated member, the guard comprising: a body including: a proximal end and a distal end opposite the proximal end, and the proximal end configured to connect to the surgical device; an interior surface defining a bore extending between the proximal end and the distal end and the bore adapted to receive the elongated member therethrough, and the interior surface configured to receive a friction reduction element for retaining the elongated member; an exterior surface extending between the proximal end and the distal end and encompassing the interior surface between the proximal end and the distal end; and at least one thermal mitigation channel located between the interior and exterior surfaces adjacent the friction reduction element and opening through at least one port in the exterior surface.

According to a fourth aspect, a surgical device is provided comprising the guard of any preceding aspect.

According to a fifth aspect, a robotic system is provided comprising a surgical device comprising the guard of any preceding aspect; and a surgical manipulator comprising a plurality of links and joints being configured to support the surgical device.

Any of the above aspects can be utilized individually, or in combination.

Any of the above aspects can be utilized with any of the following implementations:

In one implementation, the body is monolithic. In another implementation, the body is comprised of multiple parts, and is not monolithic. In one implementation, the thermal mitigation channel is defined in a substantially annular configuration about the bore. In one implementation, the at least one thermal mitigation channel comprises at least two thermal mitigation channels spaced from one another and located between the interior and exterior surfaces, with the body further comprising an intermediate wall extending between adjacent thermal mitigation channels. In one implementation, the intermediate wall defines a hole extending therethrough to fluidly connect the adjacent thermal mitigation channels. In one implementation, the thermal mitigation channels are staggered between the proximal and distal ends. In one implementation, the port connects to one of the thermal mitigation channels. In one implementation, the port connects to a plurality of the thermal mitigation channels. In one implementation, the exterior surface and each of the thermal mitigation channels have an arcuate configuration.

In one implementation, the exterior surface defines a passage adjacent one of the proximal and distal ends of the body, with the thermal mitigation channel opening through both the port and the passage. In one implementation, the at least one thermal mitigation channel comprises a proximal thermal mitigation channel adjacent the proximal end of the body and a distal thermal mitigation channel adjacent the distal end of the body and separated from the proximal thermal mitigation channel. In one implementation, the interior surface is configured to receive a friction reduction element for axially retaining the elongated member, with the at least one thermal mitigation channel located between the interior and exterior surfaces adjacent the friction reduction element. In one implementation, the friction reduction element is arranged as a sleeve disposed within the bore and coupled to the interior surface. In one implementation, the sleeve defines a hole extending therethrough and concentric with the bore, with the hole having a diameter less than a diameter of the bore for spacing the elongated member from the interior surface and supporting the elongated member with the sleeve. In one implementation, the sleeve is further defined as a bushing. In one implementation, the bushing is disposed at the distal end of the body. In one implementation, the sleeve is further defined as a bearing. In one implementation, the bearing is disposed at the proximal end of the body.

In one implementation, the elongated member is cylindrical shaft, a planar blade body, a non-cylindrical shaft, a wire, a nickel titanium (Nitonal) tool, a linkage, a flexible member, any multi-component mechanism, and the like. In one implementation, the bore has a circular-cross section and straight-cylindrical shape, or other cross-sections, such as oval, rectangular, polygonal, or the like.

In one implementation, the body is formed, in part, or in whole, by additive manufacturing. In one implementation, the at least one port is further defined as a plurality of ports arranged as an array on the exterior extending the length of the at least one thermal mitigation channel. In one implementation, the at least one port has a teardrop configuration.

In one implementation, a surgical device comprises the guard. In one implementation, the surgical device is a robotic device, such as a robotic manipulator arm comprising. plurality of links and joints or a hand-held robotic manipulator. The tool can comprise a shaft, a planar design, wire, or flexible member. The energy applicator can be a cutting bur, saw blade, saw blade cartridge, bone saw, sagittal saw, a drill bit such as for forming holes or driving a component, a reamer, an impactor, an ultrasonic tool, or the like. Within the guard, the tool and/or energy applicator can be driven rotatably, linearly, axially, flexibly, transversely, laterally, or any combination thereof.

In one implementation, the guard, exterior surface, interior surface, body, and/or bore are curved, angled, or irregularly shaped between the proximal and distal ends or along a portion between the proximal and distal ends.

In one implementation, an irrigation system is configured to connect to the guard. In one implementation, the irrigation system is configured to transfer fluid through the thermal mitigation channel(s).

BRIEF DESCRIPTION OF THE DRAWINGS

Advantages of the present disclosure will be readily appreciated as the same becomes better understood by reference to the following detailed description when considered in connection with the accompanying drawings wherein:

FIG. 5 is an elevational view of the guard of FIG. 2.

FIG. 6 is a cross-sectional view of the guard shown in FIG. 5.

DETAILED DESCRIPTION

I. Robotic System Overview

Referring to the Figures, wherein like numerals indicate like or corresponding parts throughout the several views, a system 10 (hereinafter "system") is shown throughout.

Figure 1:
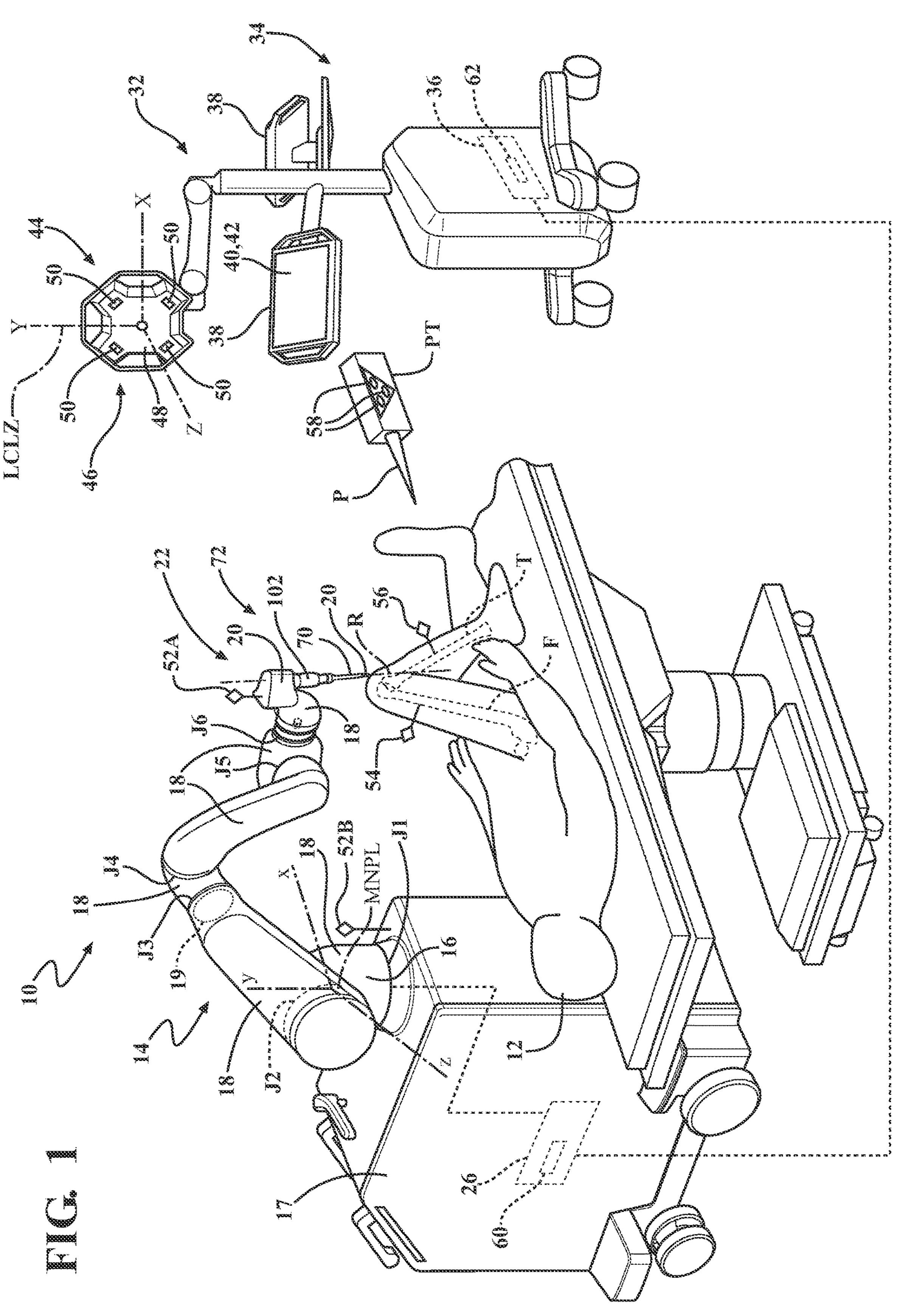
FIG. 1 is a perspective view of a robotic system for manipulating a target tissue of a patient with a tool, according to one example.

As shown in FIG. 1, the system 10 may treat an anatomy (surgical site) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves joint surgery, such as partial or total knee or hip replacement surgery, or total, partial, or reverse shoulder arthroplasty. In one example, the system 10 is designed to cut away material to be replaced by surgical implants, such as joint implants, e.g., shoulder, hip, and knee implants, including unicompartmental, bicompartmental, multicompartmental implants. Some of these types of implants are shown in U.S. Pat. No. 9,937,058, entitled, "Prosthetic Implant and Method of Implantation," the disclosure of which is hereby incorporated by reference. The system 10 and method disclosed herein may be used to perform other procedures, surgical or non-surgical, or may be used in industrial applications or other applications where robotic systems are utilized.

The system 10 may include a robotic manipulator 14. In the example shown, the robotic manipulator 14 has a base 16 and plurality of links 18. A manipulator cart 17 supports the robotic manipulator 14 such that the robotic manipulator 14 is fixed to the manipulator cart 17. The links 18 collectively form one or more arms of the robotic manipulator 14. The robotic manipulator 14 may have a serial arm configuration (as shown in FIG. 1) or a parallel arm configuration. In other examples, more than one robotic manipulator 14 may be utilized in a multiple arm configuration. The robotic manipulator 14 may comprise a plurality of (prismatic and/or rotating) joints (J) and a plurality of motor and/or joint encoders 19 located at the joints (J) for determining position data of the joints (J). For simplicity, only one joint encoder 19 is illustrated in FIG. 1, although it is to be appreciated that the other joint encoders 19 may be similarly illustrated. The robotic manipulator 14 according to one example has six joints (J1-J6) implementing at least six-degrees of freedom (DOF) for the robotic manipulator 14. The robotic manipulator 14 may have any number of degrees of freedom and may have any suitable number of joints (J) and redundant joints (J).

A surgical tool 20 (hereinafter "tool") couples to the robotic manipulator 14 and is movable relative to the base 16 to interact with the anatomy in certain modes. The tool 20 is or can form part of an end effector 22. The tool 20 may be grasped by the operator. One exemplary arrangement of the robotic manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The robotic manipulator 14 and the tool 20 may be arranged in alternative configurations. The tool 20 can be like that shown in U.S. Pat. No. 9,566,121, filed on Mar. 15, 2014, entitled, "End Effector of a Surgical Robotic Manipulator," hereby incorporated by reference.

In some examples, the robotic manipulator 14 can be a hand-held manipulator where the base is a base portion of a tool (e.g., a portion held free-hand by the user against the force of gravity) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined. Such a hand-held manipulator can be like that shown in U.S. Pat. No. 9,707,043, filed on Aug. 31, 2012, entitled, "Surgical Instrument Including Housing, A Cutting Accessory that Extends from the Housing and Actuators that Establish the Position of the Cutting Accessory Relative to the Housing," and in PCT application No. PCT/US2020/042128, entitled "Robotic Hand-Held Surgical Instrument Systems and Methods", filed on Jul. 15, 2020, the entire contents of both of which are hereby incorporated by reference.

The tool 20 includes an energy applicator 24 designed to contact the target site, such as the tissue of the patient 12 at the surgical site. The energy applicator 24 may be a rotary cutting bur, drill, saw blade, impactor, reamer, ultrasonic vibrating tip, or the like. In one example, the energy applicator 24 is specifically a rotary cutting bur.

The system 10 includes a controller 30. The controller 30 includes software and/or hardware for controlling the robotic manipulator 14. The controller 30 directs the motion of the robotic manipulator 14 and controls a state (position and/or orientation) of the tool 20 with respect to a coordinate system of the manipulator 14.

As shown in FIG. 1, the system 10 may further include a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the robotic manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. First and second input devices 40, 42 may be used to input information into the navigation computer 36 or otherwise to select/control certain aspects of the navigation computer 36. As shown in FIG. 1, such input devices 40, 42 include interactive touch-screen displays. The input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof. The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The navigation system 32 includes one or more trackers. In one example, the trackers include a pointer tracker PT, one or more manipulator trackers 52, a first patient tracker 54, and a second patient tracker 56. In the illustrated example of FIG. 1, the manipulator tracker 52 is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the robotic manipulator 14, in addition to, or other than the tool 20, such as the base 16 (i.e., tracker 52B), or any one or more links 18 of the robotic manipulator 14. The trackers 52, 54, 56, PT may be fixed to their respective components in any suitable manner. Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized. The localizer 44 tracks the trackers 52, 54, 56 to determine a state of each of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the navigation system 32 is shown in the Figures, the navigation system 32 may have any other suitable configuration for tracking the robotic manipulator 14 and the patient 12. In one example, the navigation system 32 and/or localizer 44 are ultrasound-based. In another example, the navigation system 32 and/or localizer 44 are radio frequency (RF)-based. The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

The controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the robotic manipulator 14. In one example, as shown in FIG. 1, the manipulator controller is implemented on the manipulator computer 26. The manipulator controller 60 may receive and process data from a single source or multiple sources. The controller 30 further includes a navigation controller 62 for communicating the state data relating to the femur F, tibia T, and robotic manipulator 14 to the manipulator controller 60. The manipulator controller 60 receives and processes the state data provided by the navigation controller 62 to direct movement of the robotic manipulator 14. In one example, as shown in FIG. 1, the navigation controller 62 is implemented on the navigation computer 36. The manipulator controller 60 or navigation controller 62 may also communicate states of the patient 12 and robotic manipulator 14 to the operator by displaying an image of the femur F and/or tibia T and the robotic manipulator 14 on the one or more displays 38. The manipulator computer 26 or navigation computer 36 may also command display of instructions or request information using the display 38 to interact with the operator and for directing the robotic manipulator 14.

II. Guard for a Tool

Referring to the Figures, wherein like numerals indicate like or corresponding parts throughout the several views, a guard 70 for the tool 20 is generally shown in FIGS. 2-11. The tool 20 is configured to be driven by a surgical device 72. The surgical device 72 may comprise the guard 70. Furthermore, the mechanically grounded or hand-held robotic system 10 (mentioned above) may comprise the surgical device 72 (comprising the guard 70) and a plurality of links 18 and joints J configured to support the surgical device 72, as shown in FIG. 1. The surgical device 72 may be further defined as the end effector 22 (described above). The surgical device 72 may be a powered handpiece or any other suitable component.

Figure 2:
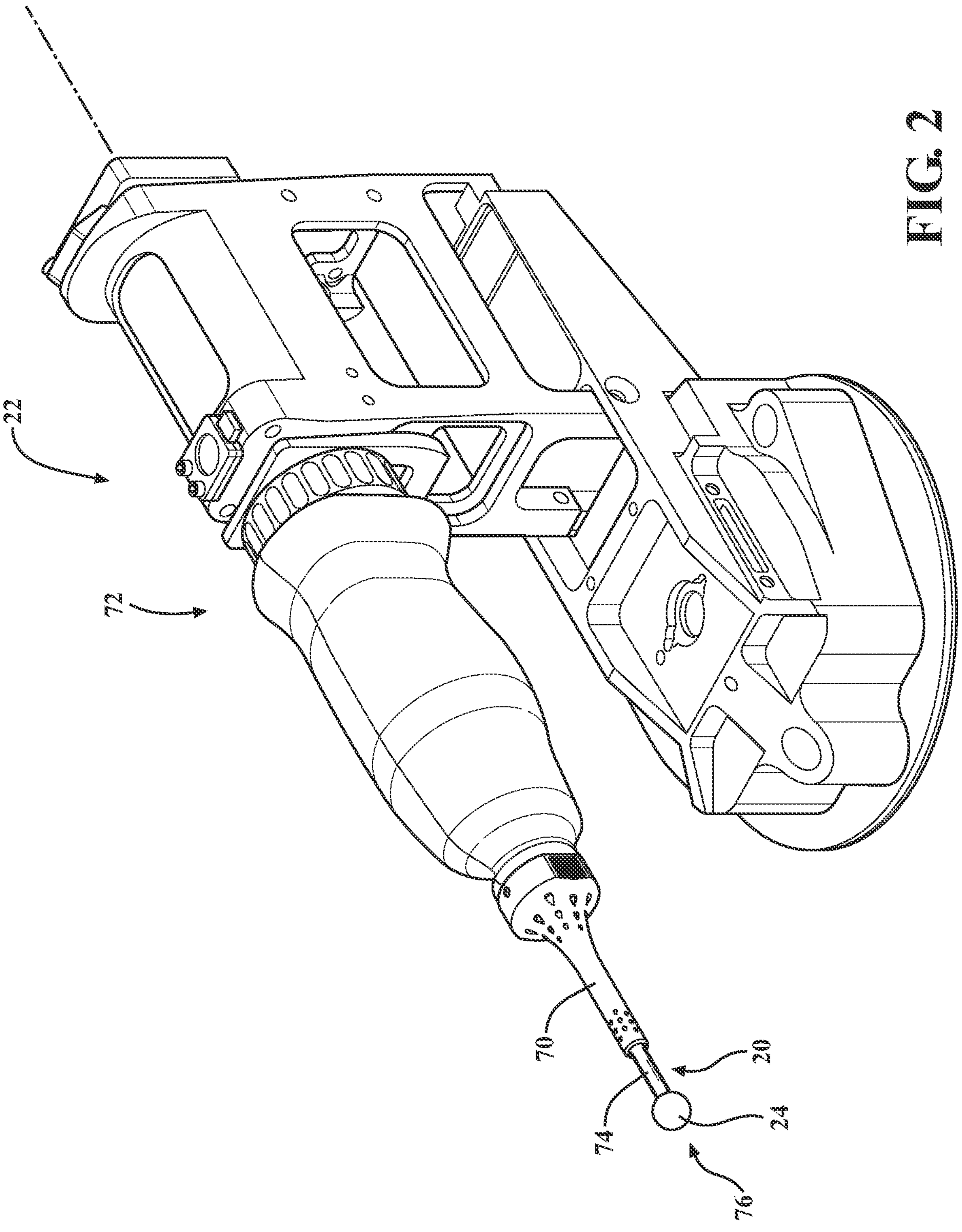
FIG. 2 is a perspective view of an end effector for use with the robotic system shown in FIG. 1, according to one example, and showing a tool and a guard.

The tool 20, in one implementation, comprises an elongated member 74 and the energy applicator 24 disposed at a distal end 76 of the elongated member 74. The elongated member in FIG. 2 is a cylindrical shaft. In other examples, the elongated member 74 can be a planar blade body, a non-cylindrical shaft, a wire, a nickel titanium (Nitonal) tool, a linkage, a flexible member, any multi-component mechanism, and the like. In the implementation of FIG. 2, the tool 20 is configured to be rotatably driven by the surgical device 72 and the energy applicator 24 is shown as a rotary bur configured to abrade and/or resect bone and tissue. The energy applicator 24 can be other rotary types of accessories, such as a drill bit, reamer, or the like. The tool 20 and/or energy applicator 24 may be disposed in a planar (e.g., blade) configuration. The tool 20 and/or energy applicator 24 may be any other suitable device for transmitting energy. In another implementation, the tool 20 is configured to be linearly driven by the surgical device 72. For example, the energy applicator 24 can be linearly extended or reciprocated along an axis of the tool 20. The linearly driven tool 20 can be a surgical saw, drill bit, prosthesis impactor or installer, cutter, cauterizer, ablator, stapler, endoscope, or the like. The tool 20 can also be reciprocated transverse to the tool axis.

As shown in FIGS. 3-6 and 11, the guard 70 may comprise a body 78. The body 78 may include a proximal end 80 and a distal end 82 opposite the proximal end 80. The proximal end 80 is configured to connect to the surgical device 72. The proximal end 80 may be configured to be coupled to the surgical device 72 through connection elements (e.g., pins) engaging both the body 78 and the surgical device 72.

Figure 11:
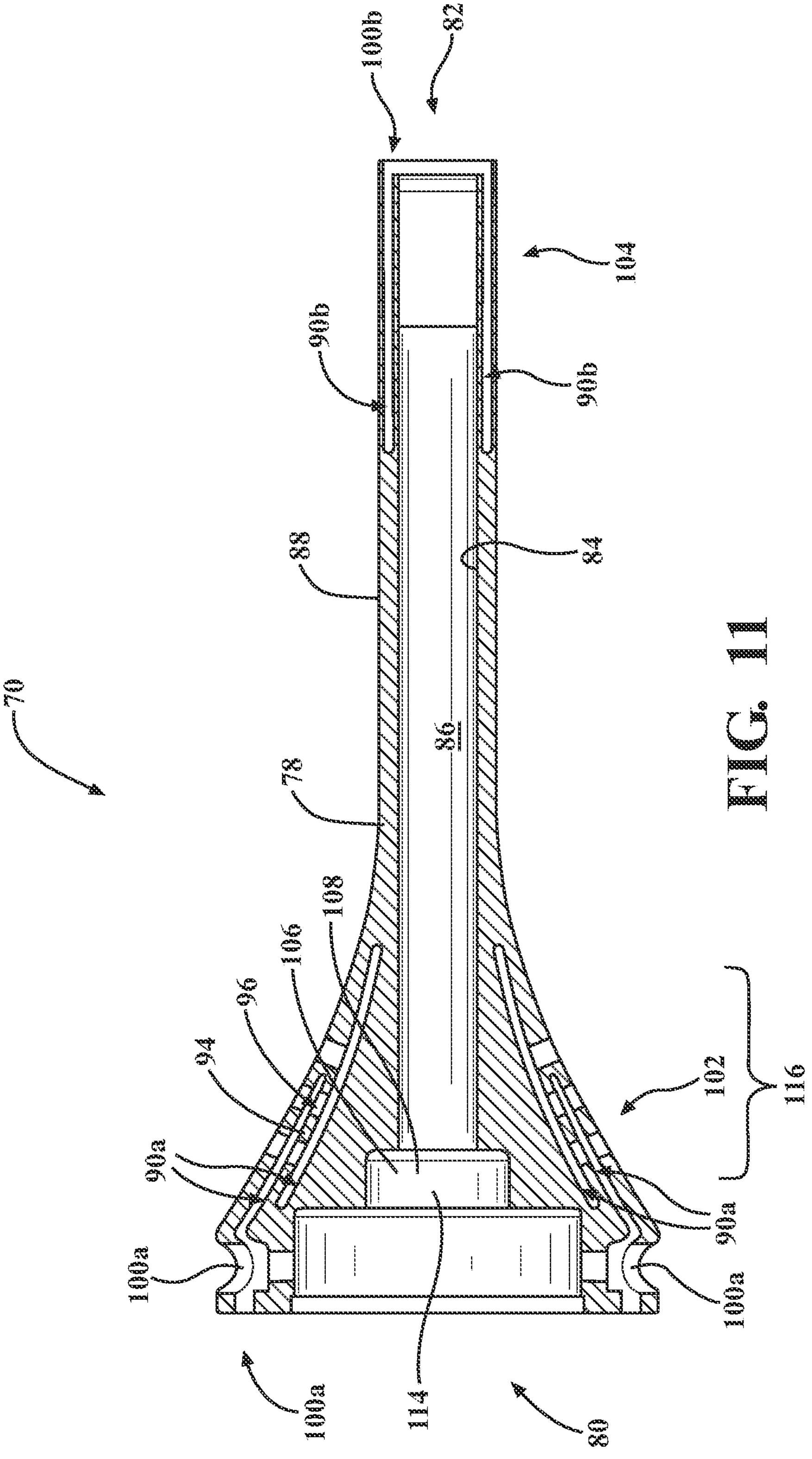
FIG. 11 is a cross-sectional view of a guard having thermal mitigation channels that are staggered.

As shown in FIGS. 6 and 11, the body 78 may further include an interior surface 84 defining a bore 86 extending between the proximal and distal ends 80, 82. The bore 86 may be adapted to receive the elongated member 74 therethrough. The bore 86 shown in the Figures has a circular-cross section and straight-cylindrical shape. The bore 86 can have any other suitable shape or cross-section, such as oval, rectangular, polygonal, or the like. For example, the bore 86 can be formed in a slot configuration to accommodate a tool such as a planar saw. In some implementations, the bore 86 can be curved, angled, bent, or irregularly formed along the length of the body 78. In other words, the bore 86 need not necessarily be straight between the proximal and distal ends 80, 82 of the body 78. In such configurations, the body 78 of the guard 70, for example at the distal end 80, can similarly comprise a curved, angled, bent, or irregularly formed shape accommodating the bore 86. When the bore 86 is not straight, the elongated member 74 can be flexible to enable the tool 20 to be actuated within the bore 86.

The body 78 may further comprise an exterior surface 88 extending between the proximal and distal ends 80, 82 and encompassing the interior surface 84 between the proximal and distal ends 80, 82, and at least one thermal mitigation channel 90*a*, 90*b* located between the interior and exterior surfaces 84, 88 and opening through at least one port 92 in the exterior surface 88.

As shown in FIGS. 7-10, the thermal mitigation channel 90*a*, 90*b* may be defined in a substantially annular configuration about the bore 86. Said differently, the thermal mitigation channel 90*a*, 90*b* may be concentric with the bore 86. As such, the exterior surface 88 and each of the thermal mitigation channels 90*a*, 90*b* may have an arcuate configuration. The thermal mitigation channel 90*a*, 90*b* may be disposed in any suitable shape and in any suitable arrangement relative to the bore 86 to facilitate heat transfer away from the bur.

Actuation of the tool 20 within the bore 86 of the guard 70 generates heat. This actuation of the tool 20 can be such as, but not limited to: rotary, linear or non-linear, lateral, axial, radial, transverse, helical, or any combination thereof. More specifically, contact between the tool 20 and the guard 70 (or components therein) may generate heat during actuation due to friction therebetween. Furthermore, the energy applicator 24 itself may generate heat (e.g., through contact a bone), which may propagate into the elongated member 74 within the bore 86. As can be understood from the above, several problems of conventional guards are solved by the guard 70 described herein. The guard 70 prevents contact between the actuating tool 20 and the patient, staff, or surgeon. The guard 70 provides support/stiffness to the tool 20 to prevent the tool 20 from deforming/deflecting out of a tolerable precision/accuracy. The guard 70 is also configured to provide thermal mitigation (or thermo-insulation). In one example, the guard 70 enables the dissipation of and/or insulation from heat produced by the tool 20 to protect the safety of the patient and the surgeon, and to protect the operability and longevity of the tool 20, the guard 70, and the surgical device 72. As will be described below, thermal mitigation channel(s) and the port(s) enable a fluid, such as gas (e.g., air) to move away from the bore and out of the guard 70. The fluid absorbs heat generated by the actuation of the tool and dissipates the heat into the external air, which cools the guard. The thermal mitigation channel(s) and the port(s) also provide a longer path for propagation of heat to provide cooling to the guard 70. Thermal mitigation for the guard 70 reduces the chance of burns and tissue damage to the patient, staff and/or operator. Furthermore, removing the heat wear and tear on the tool, the guard, and the surgical device, improving the longevity of those devices. Accordingly, the guard 70 provides multiple advantages of thermal isolation/mitigation/protection, tool retention, structural integrity, and reduced footprint.

Figure 7:
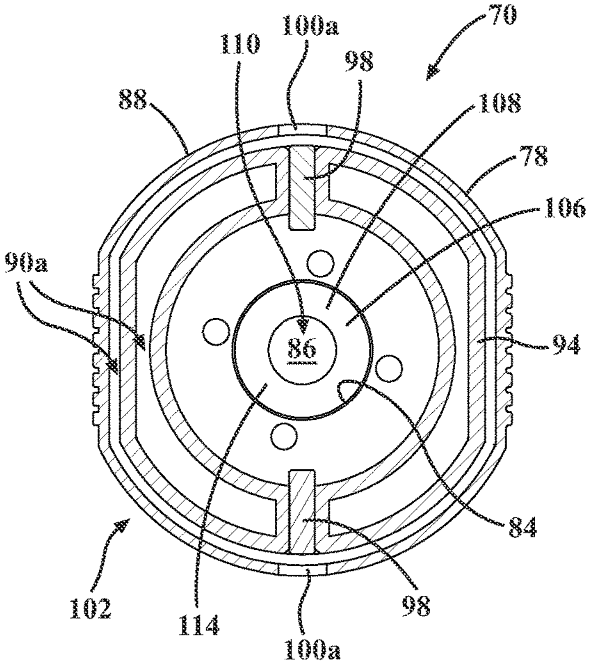
FIG. 7 is a cross-sectional view of the guard shown in FIG. 5, taken along line 7-7.
Figure 8:
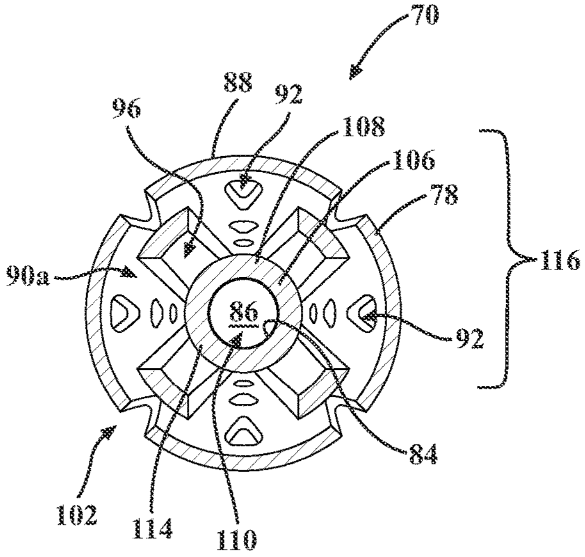
FIG. 8 is a cross-sectional view of the guard shown in FIG. 5, taken along line 8-8.
Figure 9:
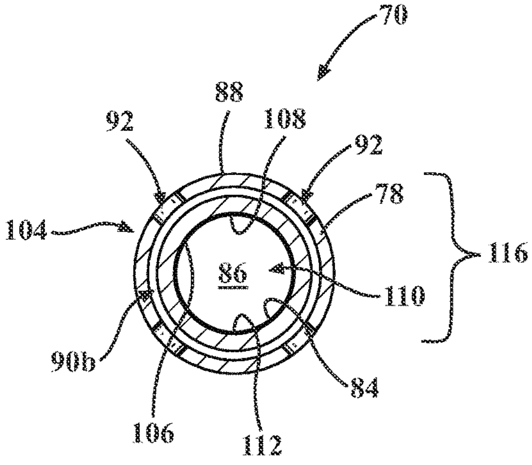
FIG. 9 is a cross-sectional view of the guard shown in FIG. 5, taken along line 9-9.
Figure 10:
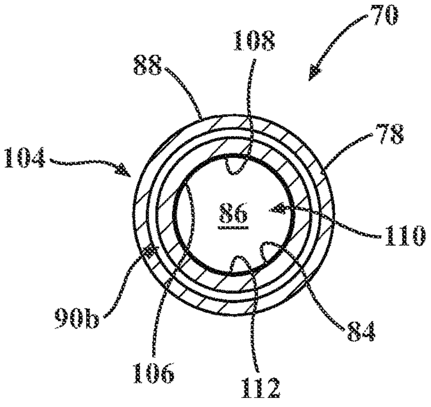
FIG. 10 is a cross-sectional view of the guard shown in FIG. 5, taken along line 10-10.

The at least one thermal mitigation channel **90*a*, 90*b* may comprise at least two thermal mitigation channels 90*a*, 90*b* spaced from one another and located between the interior and exterior surfaces 84, 88, as shown in FIGS. 6, 7, and 11. The at least two thermal mitigation channels 90*a*, 90*b* may be concentrically disposed about the bore 86 as seen at the proximal end 80 of the body 78, with one of the channels 90*a*, 90*b* disposed adjacent the interior surface 84 and with the other channel disposed adjacent the exterior surface 88. Although only two thermal mitigation channels 90*a*, 90*b* are arranged in the concentric arrangement shown in FIGS. 6, 7, and 11**, three or more may be arranged in a similar manner.

The body 78 may further comprise an intermediate wall 94 extending between adjacent thermal mitigation channels **90*a*, 90*b*. As such, the intermediate wall 94 partially defines each of the adjacent channels 90*a*, 90*b*. The intermediate wall 94 may define a hole 96 extending therethrough to fluidly connect the adjacent thermal mitigation channels 90*a*, 90*b*. Therefore, the fluid may pass between the adjacent thermal mitigation channels 90*a*, 90*b*. Moreover, the fluid warmed within the channel 90*a*, 90*b* adjacent the interior surface 84 may pass through the hole 96 and out through the port 92 to transport to cool both the bur and the guard 70**.

To support the thermal mitigation channel(s) **90*a*, 90*b*, the body 78 may comprise a plurality of ribs 98. The ribs 98 extend across the thermal mitigation channel(s) 90*a*, 90*b* to reduce distortion at the channel(s) 90*a*, 90*b* and to strengthen the guard 70**.

In one example, the thermal mitigation channels **90*a*, 90*b* are linearly aligned between the proximal and distal ends 80, 82. Said differently, the thermal mitigation channels 90*a*, 90*b* extend along essentially the same longitudinal portion of the guard 70, as seen in FIG. 6. In another example, the thermal mitigation channels 90*a*, 90*b* are staggered between the proximal and distal ends 80, 82. Said differently, at least one of the thermal mitigation channels 90*a*, 90*b* extends along a different longitudinal portion of the guard 70 than the other channel(s) 90*a*, 90*b*, as seen in FIG. 11**.

In one example, the port 92 connects to one of the thermal mitigation channels **90*a*, 90*b*. More specifically, in the example in FIG. 6, the thermal mitigation channels 90*a*, 90*b* are linearly aligned. The port 92 connects to the thermal mitigation channel 90*a*, 90*b* adjacent the exterior surface 88. When present, the hole 96 may facilitate the flow of fluid from the thermal mitigation channel(s) 90*a*, 90*b* closer to the bore 86 to the port 92. In another example, the port 92 connects to a plurality of the thermal mitigation channels 90*a*, 90*b*. More specifically, in the example in FIG. 11 showing the staggered thermal mitigation channels 90*a*, 90*b*, the port 92 is further defined as a plurality of ports 92 with ports 92 connected with different thermal mitigation channels 90*a*, 90*b***.

The exterior surface 88 may define a passage 100 adjacent one of the proximal and distal ends 80, 82 of the body 78. More specifically, the passage 100 may be disposed adjacent the proximal end 80 or distal end 82 that is adjacent the thermal mitigation channel **90*a*, 90*b*. The passage 100 may be disposed directly at the proximal or distal ends 80, 82 as shown in FIGS. 3, 4, 6, and 11, such that the passage 100 is concentrically aligned with the bore 86. The thermal mitigation channel 90*a*, 90*b* may open through both the port 92 and the passage 100. As such, the passage 100 may facilitate the flow of fluid from the thermal mitigation channel(s) 90*a*, 90*b* through either of the passage 100 and the port 92 to cool the guard 70**.

In the example shown in FIG. 6, the at least one thermal mitigation channel 90 comprises a proximal thermal mitigation channel **90*a* adjacent the proximal end 80 of the body 78 and a distal thermal mitigation channel 90*b* adjacent the distal end 82 of the body 78 and separated from the proximal thermal mitigation channel 90*a*. Therefore, the guard 70 is configured to be cooled at both the proximal and distal ends 80, 82. In this example, the passage 100 is further defined as at least one proximal passage 100*a* disposed at the proximal end 80 of the body 78 and at least one distal passage 100*b* disposed at the distal end 82 of the body 78. The proximal thermal mitigation channel 90*a* is configured to open through the proximal passage 100*a* and the distal thermal mitigation channel 90*b* is configured to open through the distal passage 100*b*. Providing the thermal mitigation channel 90*a* adjacent the proximal end 80 of the body 78 provides thermal mitigation effects at the proximal end 80. In turn, the guard 70 protects an individual who may attempt to disconnect the guard 70 from the proximal end 80 after use of the tool 20**.

As described above, the tool 20 may contact the guard 70 within the bore 86. Therefore, the friction between the tool 20 and the guard 70 generates heat as the tool 20 actuates. To facilitate effective cooling of both the guard 70 and the tool 20, the at least one thermal mitigation channel **90*a*, 90*b* may be disposed adjacent the location within the bore 86 at which the tool 20 contacts the guard 70. In the example shown in FIGS. 3-10, the tool 20 is configured to contact the guard 70 at two locations: a first region 102 adjacent the proximal end 80 and a second region 104 adjacent the distal end 82. In this example, the proximal thermal mitigation channel 90***a* is disposed adjacent the first region 102 to facilitate cooling at the first region 102 and the distal thermal mitigation channel 90*b* is disposed adjacent the second region 104 to facilitate cooling at the second region 104.

The interior surface 84 may be configured to receive a friction reduction element 106 for axially retaining the elongated member 74, with the at least one thermal mitigation channel 90*a*, 90*b* located between the interior and exterior surfaces 84, 88 adjacent the friction reduction element 106. The friction reduction element 106 may reduce the heat generated by the tool 20 through the structure of the friction reduction element 106 and/or the material of construction, as described below.

As shown in FIGS. 6-10, the friction reduction element 106 may be arranged as a sleeve 108 disposed within the bore 86 and coupled to the interior surface 84. As shown in FIG. 6, the sleeve 108 may define a hole 110 extending therethrough and concentric with the bore 86, with the hole 110 having a diameter D1 less than a diameter D2 of the bore 86 for spacing the elongated member 74 from the interior surface 84 and supporting the elongated member 74 with the sleeve 108. More specifically, the difference in diameters D1, D2 reduces the chance that the tool 20 will contact the interior surface 84 of the body 78 to ensure that the sleeve 108 receives most (if not all) of the friction from the tool 20. In the example shown in FIGS. 6-10, the sleeve 108 is press-fit into the bore 86, with the static friction between the sleeve 108 and the interior surface 84 preventing the sleeve 108 from moving longitudinally within the bore 86. The sleeve 108 may be retained within bore 86 by mechanical fastening, chemical bonding, welding, and the like.

The sleeve 108 may be further defined as a bushing 112. The bushing 112 is statically disposed within the bore 86 and acts as a lining between the tool 20 and the body 78. The bushing 112 may be configured to have a reduced coefficient friction (compared to the body 78) to reduce the heat generated as the tool 20 actuates. Furthermore, the bushing 112 may be configured to have an improved resistant to wear (compared to the body 78) to maintain contact with the tool 20 for axial support. The desired coefficient of friction and wear characteristics may be achieved through the material of construction. For example, the bushing 112 may be constructed from brass or Teflon, which are utilized for their wear resistance and reduced friction characteristics. Any other material that meets the desired characteristics may be utilized. Furthermore, the construction of the surface in contact with the tool 20 may also achieve the desired characteristics. For example, the bushing 112 may be polished to reduce friction and increase wear resistance.

In the example shown in FIG. 6, the bushing 112 is disposed at the distal end 82 of the body 78. More specifically, the bushing 112 is disposed at the second region 104. The bushing 112 may be disposed at any location within the bore 86 for supporting the tool 20. Moreover, a plurality of bushings 112 may be disposed within the bore 86 at various locations. For example, the guard 70 may include one bushing 112 located near the at the distal end 82 of the body 78 and one bushing 112 located near the proximal end 80 of the body 78. In another example, the guard 70 may include a third one bushing 112 located between the bushings near the distal end 82 and the proximal end 80, respectively.

The bushing 112 can also be a consumable or disposable or single use component that can be replaceable via regular servicing. The bushing 112 can also be part of cutting tool packaging or even integrated into the cutting tool itself as a floating or "pressed" bearing on the elongated member 74. In some instances, a cap can be used to hold the bushing 112 in position within the bore 86.

The sleeve 108 may be further defined as a bearing 114. The bearing 114 includes one surface mounted to the interior surface 84 of the body 78 and another surface mounted to the tool 20, with the surfaces of the bearing 114 rotating relative to one another through the rotation of balls, rollers, and the like disposed therebetween. The mechanical construction of the bearing 114 reduces friction between the body 78 and the tool 20.

In the example shown in FIG. 6, the bearing 114 is disposed at the proximal end 80 of the body 78. More specifically, the bearing 114 is disposed at the first region 102. The bearing 114 may be disposed at any location within the bore 86 for supporting the tool 20. Moreover, a plurality of bearings 114 may be disposed within the bore 86 at various locations. For example, the guard 70 may include one bearing 114 located near the at the distal end 82 of the body 78 and one bearing 114 located near the proximal end 80 of the body 78. In another example, the guard 70 may include a third bearing 114 located between the bearings near the distal end 82 and the proximal end 80, respectively.

Although not shown in the Figures, the tool 20 may directly contact the interior surface 84 of the body 78.

As described above, the at least one port 92 is further defined as the plurality of ports 92. The plurality of ports 92 may be arranged as an array 116 on the exterior extending the length of the at least one thermal mitigation channel 90*a*, 90*b*, as shown in FIGS. 3-6 and 11. Said differently, the ports 92 may be spaced evenly from one another across the entire length of the thermal mitigation channel 90*a*, 90*b*. Therefore, the fluid within the channel 90*a*, 90*b* may evenly enter and/or exit the thermal mitigation channels 90*a*, 90*b* through the ports 92 to ensure uniform cooling of the guard 70.

Figure 3:
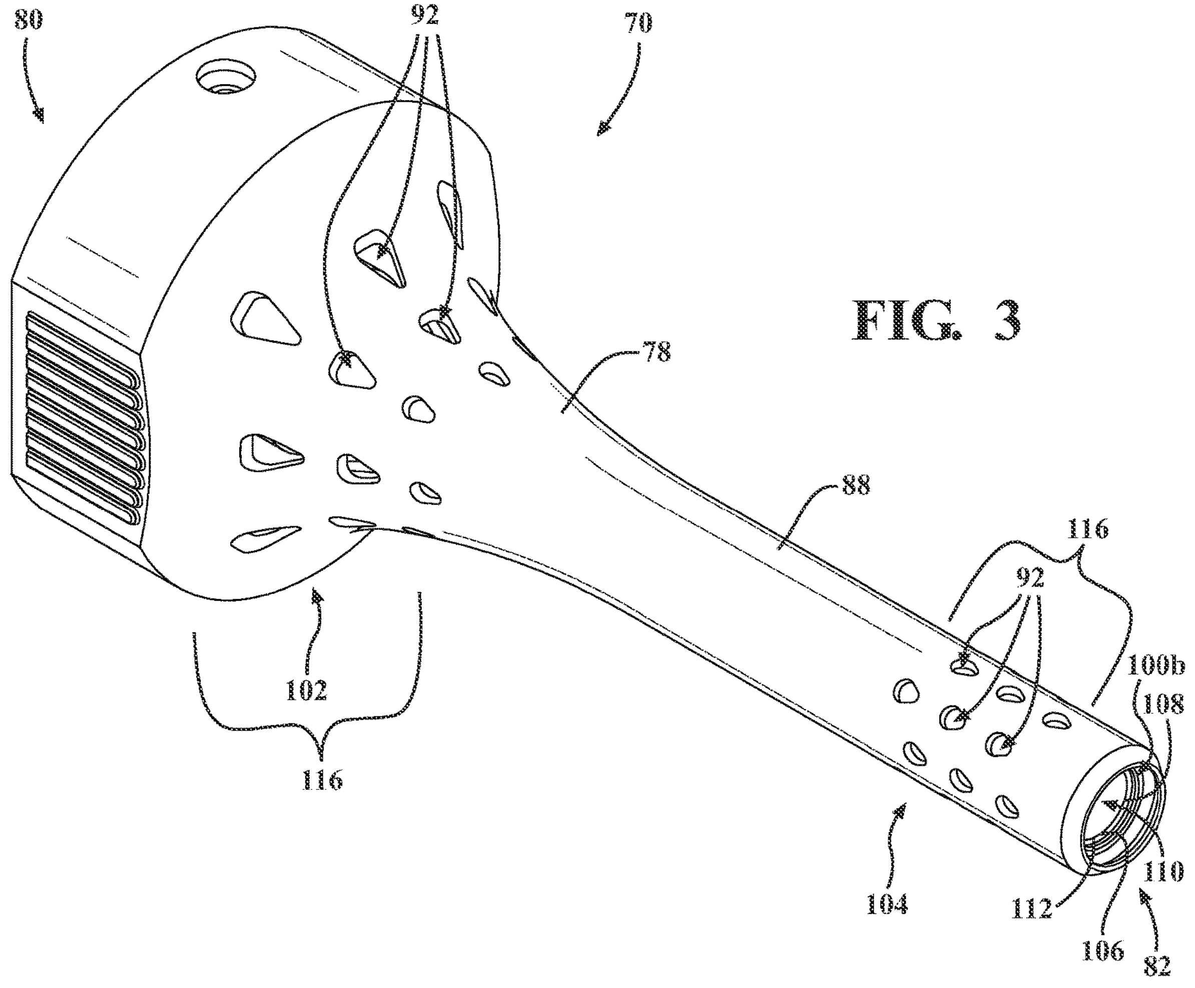
FIG. 3 is a perspective view of the guard of FIG. 2, showing a distal end.
Figure 4:
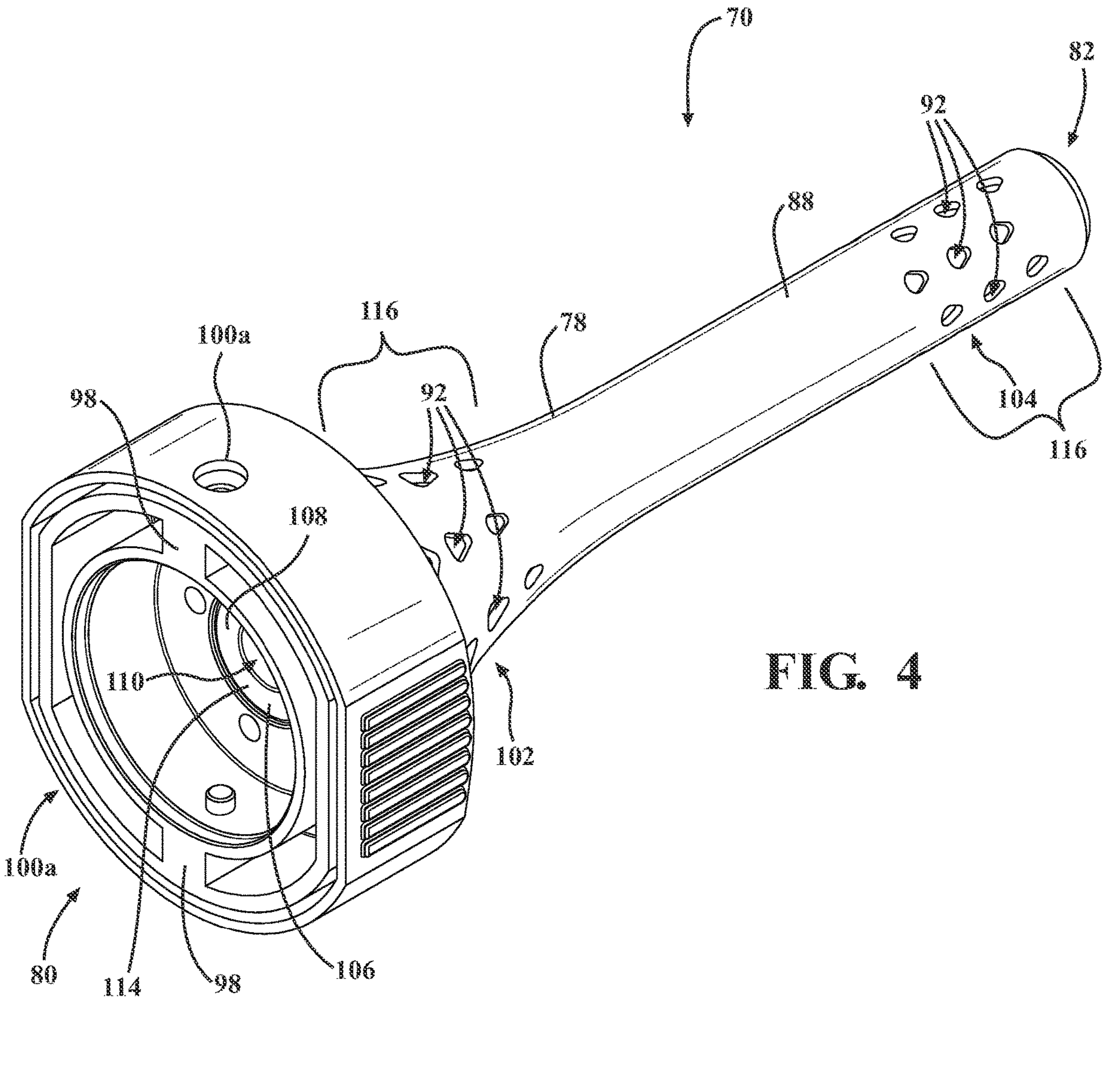
FIG. 4 is a perspective view of the guard of FIG. 2, showing a proximal end.

The at least one port 92 may be arranged in a teardrop configuration, as shown in FIGS. 3-5. The teardrop configuration may be utilized as a supported geometry for additive manufacturing of the body 78. The teardrop configuration may also improve the stiffness of the guard 70 by reducing stress risers within the material. The at least one port 92 may be arranged in a cylindrical configuration or any other suitable configuration for facilitating the transport of fluid therethrough.

The body 78 may be monolithic, i.e., integrally formed of/from a single piece or a single material, without combining multiple components together. In some examples, the body 78 is formed of a metallic material, such as aluminum. Other metals and other materials (such as polymeric, ceramic, and composite materials) may be utilized. Although the body 78 shown and described herein is monolithic, the guard 70 may be comprised of multiple components joined to form the body 78 (non-monolithic).

Whether monolithic or not, the body 78 may be formed by additive manufacturing. Additive manufacturing is the progressive deposition of layers of material to form a component and can be 3D printing or rapid prototyping. In addition to the deposition of material, additive manufacturing may also include the subsequent compaction and heating of the deposited layers, which is referred to as sintering.

In the examples shown in the Figure, the body 78 can be formed by adding material rather than removing material, referred to as subtractive manufacturing. Example subtractive manufacturing processes include cutting, milling, drilling, turning, etc. The formation of the body 78 by adding material allows for the formation of shapes and geometries that are incapable of being formed by subtractive manufacturing (or less efficiently formed by subtractive manufacturing). For example, additive manufacturing allows for the long, thin thermal mitigation channels 90*a*, 90*b* that extend substantially parallel to the bore 86. Furthermore, the curvatures and angles in the thermal mitigation channels 90*a*, 90*b* (such as near the proximal end 80 of the body 78) would be difficult to form using subtractive manufacturing. Moreover, the curvature and angles in the thermal mitigation channels 90*a*, 90*b* facilitate high stiffness despite the device's low-profile and reduced density.

In one example, the body 78 is additively manufactured by producing the proximal end 80 first. For example, the proximal end 80 may be formed such that the proximal end 80, when formed, is rested flat on a surface. Thereafter, the remainder of the body 78 can be formed (upwards) from the proximal end 80 to the distal end 82, such that the distal end 82, when formed, is above the proximal end 80. Other methods of forming the body 78 are contemplated and may depend on the type of additive manufacturing process chosen.

By using additive manufacturing of the guard 70, thermal isolation pockets can be formed to control conduction/convection relative to hot and cold regions of the body 78 while simultaneously enabling compact/low profile and structurally rigid formation of the guard 70 and its respective components. Additionally, the guard 70, having minimized thickness and dimensions, is well-suited to fit inside incision sites and not obstruct or obscure visibility or the patient target site. Additionally, the configuration of the specially designed channels and ports of the guard 70 enable cleaning and removal of contaminants. Therefore, the guard 70 is well-suited to be sterilized or autoclaved, and hence, reusable.

For any of the above implementations, it is contemplated that the guard 70, and more specifically, the thermal mitigation channels 90*a*, 90*b*, can be utilized for passing liquid therethrough. The liquid can be from any source, such as irrigation fluid (e.g., saline) or other fluid from the surgical site. For example, an irrigation system that may be part of the system 10 can be coupled to the tool 20. The irrigation system can be coupled to an irrigation pump (e.g., inside or separated from the cart 17) from which irrigation fluid transferred to the tool 20. It is possible that the irrigation fluid can be transferred directly through the guard 70. For example, the irrigation fluid can be transferred from the proximal passage 100*a*, through the proximal thermal mitigation channels 90*a*, and out of the one or more ports 92, or vice versa. The same technique can also be applied at the distal end channels and ports. The irrigation fluid can be utilized to further mitigate the thermal load. One example of an irrigation system that can be utilized with a surgical tool, such as that described herein, is described in U.S. Pat. No. 10,675,050, entitled "End effector with Liquid Delivery System", the entire contents of which are hereby incorporate by reference.

Several examples have been described in the foregoing description. However, the examples discussed herein are not intended to be exhaustive or limit the disclosure to any particular form. The terminology, which has been used, is intended to be in the nature of words of description rather than of limitation. Many modifications and variations are possible in light of the above teachings and the disclosure may be practiced otherwise than as specifically described.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A guard for a rotary tool, the rotary tool being configured to be rotatably driven by a surgical device and the rotary tool comprising an elongated member and an energy applicator disposed at a distal end of the elongated member, the guard comprising:

a body including:

a proximal end and a distal end opposite the proximal end, the proximal end configured to connect to the surgical device, and a longitudinal portion located between the proximal end and the distal end;

an interior surface defining a bore extending between the proximal end and the distal end and the bore adapted to receive a friction reduction element configured to retain the elongated member therethrough, and the friction reduction element defining a first longitudinal length;

an exterior surface extending between the proximal end and the distal end and encompassing the interior surface between the proximal end and the distal end; and at least one thermal mitigation channel located between the interior surface and the exterior surface adjacent to the friction reduction element and extending a second longitudinal length spanning at least the first longitudinal length, the at least one thermal mitigation channel opening through a plurality of ports arranged as an array on the exterior surface, the array being located on the longitudinal portion and being arranged within the second longitudinal length, wherein the at least one thermal mitigation channel and the plurality of ports are configured to dissipate heated air or gas from the body in response to the rotary tool being rotatably driven; and wherein the longitudinal portion includes a segment adjacent to and non-overlapping the at least one thermal mitigation channel, the segment comprising solid material fully extending between the interior and exterior surface.

2. The guard as set forth in claim 1, wherein the at least one thermal mitigation channel is defined in a substantially annular configuration about the bore.

3. The guard as set forth in claim 1, wherein the at least one thermal mitigation channel comprises two thermal mitigation channels spaced from and adjacent to one another and located between the interior surface and the exterior surface, with the body further comprising an intermediate wall extending between the two thermal mitigation channels.

4. The guard as set forth in claim 3, wherein the intermediate wall defines a hole extending therethrough to fluidly connect the two thermal mitigation channels and wherein the plurality of ports fluidly connects to at least one of the two thermal mitigation channels.

5. The guard as set forth in claim 3, wherein the two thermal mitigation channels are staggered between the proximal end and the distal end.

6. The guard as set forth in claim 1, wherein the exterior surface defines a passage adjacent one of the proximal end and the distal end of the body, with the at least one thermal mitigation channel opening through both of the plurality of ports and the passage.

7. The guard as set forth in claim 1, wherein the at least one thermal mitigation channel comprises a proximal thermal mitigation channel adjacent the proximal end of the body and a distal thermal mitigation channel adjacent the distal end of the body and separated from the proximal thermal mitigation channel.

8. The guard as set forth in claim 1, wherein the second longitudinal length is greater than the first longitudinal length.

9. The guard as set forth in claim 1, wherein the friction reduction element is arranged as a sleeve disposed within the bore and coupled to the interior surface, wherein the sleeve defines a hole extending therethrough and concentric with the bore, with the hole having a diameter less than a diameter of the bore for spacing the elongated member from the interior surface and supporting the elongated member with the sleeve.

10. The guard as set forth in claim 1, wherein the body is monolithic and formed by additive manufacturing.

11. The guard as set forth in claim 1, wherein each port of the plurality of ports comprises a teardrop configuration.

12. The guard as set forth in claim 1, wherein the friction reduction element has an annular configuration and the at least one thermal mitigation channel is disposed annularly about the friction reduction element.

13. The guard as set forth in claim 1, wherein, in response to the rotary tool being rotatably driven, the at least one thermal mitigation channel and the plurality of ports are further configured to dissipate heated air or gas generated by the friction reduction element.

14. The guard as set forth in claim 1, wherein the exterior surface has an annular configuration.

15. The guard as set forth in claim 1, wherein the plurality of ports comprises at least six ports with each port being spaced apart and separated from the other ports.

16. The guard as set forth in claim 9, wherein the sleeve is further defined as a bushing or a bearing.

17. A surgical system comprising:

a rotary tool comprising an elongated member and an energy applicator disposed at a distal end of the elongated member;

a surgical device configured to receive and rotatably drive the rotary tool; and a guard for the rotary tool, the guard comprising:

a body including:

a proximal end and a distal end opposite the proximal end, the proximal end configured to connect to the surgical device, and a longitudinal portion located between the proximal end and the distal end;

an interior surface defining a bore extending between the proximal end and the distal end and the bore adapted to receive a friction reduction element configured to retain the elongated member therethrough, and the friction reduction element defining a first longitudinal length;

an exterior surface extending between the proximal end and the distal end and encompassing the interior surface between the proximal end and the distal end; and at least one thermal mitigation channel located between the interior surface and the exterior surface adjacent to the friction reduction element and extending a second longitudinal length spanning at least the first longitudinal length, the at least one thermal mitigation channel opening through a plurality of ports arranged as an array on the exterior surface, the array being located on the longitudinal portion and being arranged within the second longitudinal length, wherein the at least one thermal mitigation channel and the plurality of ports are configured to dissipate heated air or gas from the body in response to the surgical device rotatably driving the rotary tool and wherein the longitudinal portion includes a segment adjacent to and non-overlapping the at least one thermal mitigation channel, the segment comprising solid material fully extending between the interior and exterior surface.

18. A robotic system comprising:

a rotary tool comprising an elongated member and an energy applicator disposed at a distal end of the elongated member;

a surgical device configured to receive and rotatably drive the rotary tool; and a surgical robot configured to support and move the surgical device; and a guard for the rotary tool, the guard comprising:

a body including:

a proximal end and a distal end opposite the proximal end, the proximal end configured to connect to the surgical device, and a longitudinal portion located between the proximal end and the distal end;

an interior surface defining a bore extending between the proximal end and the distal end and the bore adapted to receive a friction reduction element configured to retain the elongated member therethrough, and the friction reduction element defining a first longitudinal length;

an exterior surface extending between the proximal end and the distal end and encompassing the interior surface between the proximal end and the distal end; and at least one thermal mitigation channel located between the interior surface and the exterior surface adjacent to the friction reduction element and extending a second longitudinal length spanning at least the first longitudinal length, the at least one thermal mitigation channel opening through a plurality of ports arranged as an array on the exterior surface, the array being located on the longitudinal portion and being arranged within the second longitudinal length, wherein the at least one thermal mitigation channel and the plurality of ports are configured to dissipate heated air or gas from the body in response to the surgical device rotatably driving the rotary tool and wherein the longitudinal portion includes a segment adjacent to and non-overlapping the at least one thermal mitigation channel, the segment comprising solid material fully extending between the interior and exterior surface.

* * * * *